US008486467B1

(12) United States Patent
Prescott

(10) Patent No.: US 8,486,467 B1
(45) Date of Patent: Jul. 16, 2013

(54) DERMAL FILLER AND METHOD OF USING SAME

(76) Inventor: Albert G. Prescott, Westford, MA (US)

( * ) Notice: Subject to any disclaimer, the term of this patent is extended or adjusted under 35 U.S.C. 154(b) by 219 days.

(21) Appl. No.: 12/212,692

(22) Filed: Sep. 18, 2008

Related U.S. Application Data

(60) Provisional application No. 60/973,954, filed on Sep. 20, 2007.

(51) Int. Cl.
*C07K 14/235* (2006.01)
*A61K 38/00* (2006.01)

(52) U.S. Cl.
USPC .......................... 424/780; 424/239.1; 424/401

(58) Field of Classification Search
None
See application file for complete search history.

(56) References Cited

U.S. PATENT DOCUMENTS

| | | | | | |
|---|---|---|---|---|---|
| 5,264,422 | A * | 11/1993 | della Valle et al. | ............. | 514/26 |
| 5,904,936 | A * | 5/1999 | Huille et al. | .................. | 424/489 |
| 5,906,997 | A * | 5/1999 | Schwartz et al. | ............. | 514/781 |
| 2004/0063616 | A1* | 4/2004 | Patt | .................... | 514/6 |
| 2005/0037472 | A1* | 2/2005 | Shih et al. | ..................... | 435/135 |
| 2005/0261632 | A1* | 11/2005 | Xu | ................... | 604/173 |
| 2006/0099264 | A1* | 5/2006 | Chan et al. | .................... | 424/486 |
| 2006/0127447 | A1* | 6/2006 | Sung et al. | .................... | 424/439 |
| 2006/0134140 | A1* | 6/2006 | Lasko et al. | ................ | 424/239.1 |
| 2006/0153785 | A1* | 7/2006 | Ho et al. | .......................... | 424/61 |
| 2007/0010652 | A1* | 1/2007 | Angot et al. | .................... | 528/328 |
| 2007/0071729 | A1* | 3/2007 | Bernstein | ..................... | 424/93.7 |
| 2007/0083155 | A1* | 4/2007 | Muller | ............................ | 604/91 |
| 2007/0110693 | A1* | 5/2007 | Patt | ............................. | 424/70.11 |
| 2007/0125978 | A1* | 6/2007 | Ho et al. | ........................ | 252/175 |
| 2008/0020000 | A1* | 1/2008 | McKerracher | ............. | 424/239.1 |
| 2008/0026070 | A1* | 1/2008 | Bonnet-Gonnet | ............ | 424/489 |
| 2008/0070993 | A1* | 3/2008 | Borbely | .......................... | 514/777 |
| 2008/0107744 | A1* | 5/2008 | Chu | ............................... | 424/489 |
| 2009/0203790 | A1* | 8/2009 | Yamamoto et al. | ........... | 514/561 |

FOREIGN PATENT DOCUMENTS

JP 0716360 * 6/1995

OTHER PUBLICATIONS

Olding et al (Annals of Plastic Surgery, Jul. 2005, vol. 55, No. 1, p. 25-29)(Abstract only).*
Anika Therapeutics, Inc., Summary of Safety and Effectiveness, Cosmetic Tissue Augmentation Product/ Injectable Dermal Filler, Dec. 20, 2006.
Allesandrini, A., et al., ACP gel: a new hyaluronic acid-based injectable for facial rejunvenation. Preclininal data in a rabbit model, Plast Reconstr Surg., Aug. 2006.

* cited by examiner

*Primary Examiner* — Albert Navarro
*Assistant Examiner* — Ginny Portner
(74) *Attorney, Agent, or Firm* — Brian M. Dingman; Dingman IP Law, PC

(57) ABSTRACT

Polyglutamic acid (PGA) formulations are provided for use as a dermal filler. Also provided are methods of use of such formulations for treatment of cosmetic defects.

4 Claims, No Drawings

DERMAL FILLER AND METHOD OF USING SAME

CROSS-REFERENCE TO RELATED APPLICATION

This application claims priority of Provisional application Ser. No. 60/973,954, filed on Sep. 20, 2007. The entire contents of such application are incorporated herein by reference.

FIELD OF THE INVENTION

This invention relates to dermal fillers and the aesthetics market.

BACKGROUND OF THE INVENTION

In 2002 approximately 6.6 million people in the United States underwent cosmetic procedures (both surgical and non-surgical). Of this, a number of procedures were non-surgical injections for the removal of wrinkles and various other aesthetic defects. The market for aesthetic injectables is extremely large and has grown quite quickly over the past 5 years, increasing 26% from 2003 to 2004. The injectables market is now over $2.19 billion with BOTOX® as the leader with 81% percent of all sales. These injections are comprised of various materials including Botulinum toxin (i.e., BOTOX®) and a class of materials known as facial fillers.

Facial fillers are materials that are biologically inert. They are injected subdermally into the area of concern and fill the area, thus removing unwanted facial wrinkles and other cosmetic defects. The most common fillers, and Botulinum toxin, are noted below with potential drawbacks.

In one procedure, autologous fat is removed via a mini liposuction procedure from other parts of the body such as the thighs, buttocks or stomach, and is used to fill wrinkles and contour lines. There is no concern of allergic reactions, but this is a multi-step process that is more invasive, and is more costly due to additional time in the doctor's office.

Botulinum toxin is a bacterial toxin. Serious heart problems and serious allergic reactions have been reported with its use. These symptoms include difficulty swallowing, speaking or breathing. The most common side effects following injection include temporary eyelid droop and nausea. Localized pain, infection, inflammation, tenderness, swelling, redness, and/or bleeding/bruising have also been noted.

Bovine collagen is a tissue-extracted dermal filler material that is costly and has both viral clearance issues as well as BSE (Mad Cow Disease) concerns. Allergic reactions have also been reported and thus skin tests are required.

Calcium hydroxyapatite is a common component of Bone Filler, a thick pasty material that is difficult to inject. It is typically used in conjunction with other injections and is not FDA approved, but instead is an "off-label" use.

Human collagen is more costly than Bovine collagen and difficult to obtain. No allergic reactions have been noted, but extensive testing for HIV and other viruses must be performed.

Hyaluronic acid (HA) is made from a basic element in connective skin tissue, HA gel, along with collagen, is the framework or medium that skin cells live in. Results of its use as a dermal filler indicate that it appears to last longer than collagen and human fat. The drawbacks are that HA comes from one of two sources, avian (bird) tissues extraction, and the bacteria Streptococcus pneumoniae (a human pathogen that is the chief cause of pneumonia). Allergic reactions have been noted and skin tests are required.

DESCRIPTION OF THE INVENTION

Such challenges associated with materials previously used for treatment of cosmetic defects can be overcome by using polyglutamic acid (PGA), and compounds comprising PGA, as an injectable dermal filler. PGA has some similarities to HA, however, it does have several important differences. First, PGA, though broken down by the body over time, is not native to the body. As a result, PGA tends to be resident in the body longer than other native materials such as HA and collagen, which are readily broken down in situ. Further, PGA is produced by the fermentation of a non-pathogenic bacteria. There are no viral clearance issues associated with PGA, and the host organism is not toxic to humans. As a result, PGA may be produced and used in humans for much less cost than all the other materials mentioned above. There are no known allergenic responses associated with PGA, and no known toxic issues such as those associated with Botulinum toxin.

PGA may be formulated in sterile water for delivery purposes. PGA concentration may be varied. In certain embodiments, concentrations of PGA ranging from 1-3% are appropriate for provided formulations. In some embodiments, the concentration of PGA in a formulation may be about 1% PGA, about 2% PGA, or about 3% PGA.

In some embodiments, PGA in a formulation is a high molecular weight PGA. In certain embodiments, PGA in formulations has a molecular weight above about one million daltons.

Counter-cations of different valences (e.g., sodium Na+, calcium Ca++) may be included in a formulation in order to modify residence time of the PGA gel. Counter-cations may be included in a formulation in concentrations ranging from about 0.1% to about 1%. In some embodiments, counter-cations may be included in concentrations of about: 0.2%, 0.3%, 0.4%, 0.5%, 0.6%, 0.7%, 0.8% or 0.9%. In some embodiments, a formulation of PGA may include a sodium salt. In some embodiments, a formulation of PGA may include a calcium salt. In certain embodiments, a formulation include about 0.9% NaCl. In certain embodiments, a formulation includes about 0.4% $CaCl_2$.

In addition, since PGA is biologically inactive, it may be combined with other existing treatments. In certain embodiments, a formulation may comprise an additional agent useful for treatment of a cosmetic defect. In some embodiments, a formulation may comprise PGA as well one or more additional agents, such as Botulinum toxin, autologous fat, collagen, hydroxyapatite, and hyaluronic acid.

In one embodiment, a method of treating a cosmetic defect in an individual is provided. The method comprises administering a composition comprising a PGA formulation to an individual. Administration of the composition to the individual results in treating the cosmetic defect in the individual. Compositions according to the provided PGA formulations are useful in the method.

Formulations of the invention are useful for treatment of a cosmetic defect in an individual. In some embodiments, administration of a PGA formulation may be useful for treatment of any of wrinkles, marrionette lines, glabellar lines, crow's feet, or brow furrows. In some embodiments, formulations of the invention are useful for treatment of more than one of wrinkles, marrionette lines, glabellar lines, crow's feet, or brow furrows. In certain embodiments, formulations of the invention are useful for treatment of one or more wrinkles.

In certain embodiments, administration of a formulation of the invention is delivered to an individual via a subdermal injection. When administered via subdermal injection, very small needles may be utilized. Formulations ranging from 1-3% PGA have been successfully passed through syringes having needles as small as 30 gauge. Injection of a formulation may be made at, or around the site of the cosmetic defect.

EXEMPLIFICATION

Example 1

PGA Using Preferred Fermentation Method, and Purification to Medical Grade

*Bacillus licheniformis* ATCC 9945a was grown in Medium E. The fermentation was carried out at small scale, in shake flasks, at 37 C. Aeration was provided by diffusion. When the viscosity stopped rising (typically after about 3-5 days of fermentation), the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.22 microns, to remove the host cells.

The filtrate was neutralized, and buffer exchanged with pure water and concentrated via diafiltration using a filter with a MWCO of 30 kDa. Material from this purification may be sterile filtered.

To describe the process in more detail, when the viscosity stopped rising, the fermentation broth was re-circulated through an OMEGA™ Polyethersulfon ultra-filtration cartridge by Pall Corporation with a 0.2 micron pore size. Once collected, the filtrate was re-circulated using an OMEGA™ Polyethersulfon ultra-filtration cartridge by Pall Corporation with a 0.16 micron pore size. The filtrate was collected and re-circulated through an OMEGA™ Polyethersulfon ultra-filtration cartridge by Pall Corporation with a 30 kda MWCO pore size. Five diafiltration volumes of solution were processed. At the end, the retentate was collected, sterilized by passing through a 0.22 micron filter, and precipitated in sterile ethanol and stored.

Material from this example has been used in rats in subsequent experiments with no inflammatory response. The molecular weight was determined to be 2 million Daltons using the following analytical MALLS method described in the Stock thesis that is incorporated by reference herein. PGA was dissolved at a concentration of 1 mg/ml in 0.1M citric acid, pH 2 to 3, with 0.05% sodium azide. The sample was degassed and 0.2 milliliters was injected at a flow rate of 0.5 mls/min. The SEC can utilize a TOSOHAAS™ TSK G5000PWXL, G6000PWXL, WATERS™ Ultrahydrogel 1000 or 250. A DAWN™ DSP laser photometer from Wyatt technologies in conjunction with a WATERS™ differential refractometer is used for detection.

This process is capable of making high molecular weight (when measured as described) poly-gamma-glutamic acid at purities up to and including pharmaceutical grade.

Example 2

PGA from Another Commercial Source Purified

A sample reported to be poly-gamma-glutamic acid in excess of 1 million Daltons was received from an offshore commercial supplier. The viscosity of a sample of known concentration seemed to be lower than would be the case if the PGA was indeed of the reported molecular weight. Analysis was impossible due to the large amount of contaminants, as evidenced by the off-white color noted when the sample was hydrated, and the fact that the hydrated sample had an odor similar to fermentation broth.

This material was re-circulated through an OMEGA™ Polyethersulfon ultra-filtration cartridge by Pall Corporation with a 0.2 micron pore size. Once collected, the filtrate was re-circulated using an OMEGA™ Polyethersulfon ultra-filtration cartridge by Pall Corporation with a 0.16 micron pore size. The filtrate was collected and re-circulated through an OMEGA™ Polyethersulfon ultra-filtration cartridge by Pall Corporation with a 30 kda MWCO pore size. Five diafiltration volumes of solution were processed. The resulting material was clear and odorless, supporting the production of low molecular weight, high purity PGA.

Example 3

PGA

*Bacillus licheniformis* ATCC 9945a was grown in Medium E. The fermentation was carried out at small scale, in shake flasks, at 37 C. Aeration was provided by diffusion. When the viscosity stopped rising, the fermentation broth was buffer exchanged via diafiltration using a filter with a molecular weight cut off (MWCO) of 30 kDa. The mixture of cells and PGA was then buffered in citric acid, and micro-filtered using a filter with an opening of 0.16 microns.

The filtrate was neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 4

PGA

*Bacillus licheniformis* ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by passing the broth through a 0.22 micron TFF filter and collecting the filtrate. The filtrate was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 5

PGA

*Bacillus licheniformis* ATCC 9945a was grown in Medium E. The fermentation was carried out at small scale, in shake flasks, at 37 C. Aeration was provided by diffusion. When the viscosity stopped rising, the pH of the fermentation broth was lowered to 2 by the addition of HCl. The cells were then removed by centrifugation at a speed over 10,000×g. The supernatant was then neutralized, and buffer exchanged with pure water and concentrated via diafiltration using a filter with a MWCO of 30 kDa. Material from this purification may be sterile filtered. Material from this example has been used in rats in subsequent experiments with no inflammatory response. The molecular weight was determined to be 2 million Daltons using the method described above in conjunction with example 1.

Example 6

PGA Formulated for Treating Defects

PGA prepared according to Example 4 was sterile filtered and transferred to sterile containers and lyophilized overnight. Lyophilized PGA was then added to various amounts of water that was 0.9% NaCl, such that 1%, 2%, and 3% PGA solutions were obtained. The same formulations were repeated with water that was 0.4% $CaCl_2$. All formulations were tested to ensure they could be expelled through a 30 gauge syringe.

The above test was repeated, with the only change being that the 0.9% NaCl and 0.4% $CaCl_2$ solutions were buffered at pH 7.0 with a standard phosphate buffer. These formulations were also successfully expelled through a 30 gauge needle.

Example 7

Pre-Clinical Studies 1 ml of calcium PGA (The PGA was made per example 3 and then sterilized, lyophilized and reconstituted with a 0.4% calcium chloride solution per example 6. The sample had a concentration of about 3% PGA and comprised about 0.4% calcium chloride. The PGA had a MW of about 1.26 million daltons), was injected subdermally in two separate locations on two different rabbits. Forty-eight hours post-injection, the subcutaneous flap was removed. A scalpel and syringe were used to remove the depot of injected material that was still resident in the dermal space. The material was weighed and compared to the amount injected. In one rabbit, 76% of the material remained, and in the second, 77% remained. This compares to about 21-23% two-day retention in reported comparable tests of human collagen dermal filler, and indicates the slow degradation that is useful in a dermal filler material.

What is claimed is:

1. A method of treating a cosmetic defect in an individual, comprising:
    a) formulating a water-based solution consisting of:
        i) bacterially-produced polyglutamic acid (PGA) having a molecular weight above about 1 million Daltons, the PGA at a concentration of from about 1% to about 3%; and
        ii) from about 0.1% to about 1% of a counter cationic salt; and
    b) subdermally injecting the solution proximate a cosmetic defect that is selected from the group consisting of wrinkles, marrionette lines, glabellar lines, crow's feet, brow furrows, and combinations thereof, thereby treating the cosmetic defect in the individual.

2. The method of claim 1 in which the cationic species comprises calcium.

3. The method of claim 2, wherein the composition further comprises an agent selected from the group of agents consisting of a Botulinum toxin, autologous fat, collagen, hydroxyapatite, and hyaluronic acid.

4. The method of claim 3, wherein the injection is accomplished using a needle of about 30 gauge.

* * * * *